United States Patent
Eggenweiler et al.

(10) Patent No.: US 6,531,498 B1
(45) Date of Patent: Mar. 11, 2003

(54) ISOXAZOLE DERIVATIVES TO BE USED AS PHOSPHODIESTERASE VII INHIBITORS

(75) Inventors: Hans-Michael Eggenweiler, Weiterstadt (DE); Rochus Jonas, Darmstadt (DE); Michael Wolf, Darmstadt (DE); Michael Gassen, Griesheim (DE); Thomas Welge, Alsbach (DE)

(73) Assignee: Merck Patentgesellschaft, Darmstadt (DE)

( * ) Notice: Subject to any disclaimer, the term of this patent is extended or adjusted under 35 U.S.C. 154(b) by 0 days.

(21) Appl. No.: 10/129,270

(22) PCT Filed: Oct. 18, 2000

(86) PCT No.: PCT/EP00/10239

§ 371 (c)(1),
(2), (4) Date: May 3, 2002

(87) PCT Pub. No.: WO01/32175

PCT Pub. Date: May 10, 2001

(30) Foreign Application Priority Data

Nov. 4, 1999  (DE) .......................................... 199 53 024

(51) Int. Cl.$^7$ ...................... C07D 261/06; A61K 31/42; A61P 43/00
(52) U.S. Cl. ...................... 514/378; 548/247; 548/248; 548/249
(58) Field of Search ................................ 548/247, 248, 548/249; 514/378

(56) References Cited

FOREIGN PATENT DOCUMENTS

| | | |
|---|---|---|
| EP | 0633254 | 1/1995 |
| WO | 95/14680 | 6/1995 |
| WO | WIPO 9514680 | 6/1995 |
| WO | 95/14681 | 6/1995 |
| WO | WIPO 9514681 | 6/1995 |

OTHER PUBLICATIONS

Database Chemcats Online!. Aug. 23, 1999, retrieved from STN Database Accession No. 2001 326337 to 343. 359, 366, 367, 377 378 XP002163572.

Database Registry Online!. Chemical Library. retrieved from STN XP002163573.

Fischer et al, J. Prakt. Chem. (1998), 330(6), 981–92 CAS Abstract Only.*

Database Chemcats Online! Aug. 23, 1999, retrieved from STN Database Accession No 2001 326337 to 343; 359, 366, 367, 377 378 XP002163572.

Database Registry Online! Chemical Library, retrieved from STN XP002163573.

* cited by examiner

*Primary Examiner*—Joseph K. McKane
*Assistant Examiner*—Kamal Saeed
(74) *Attorney, Agent, or Firm*—Millen, White, Zelano & Branigan, P.C.

(57) ABSTRACT

The invention relates to compounds of formula I and to their physiologically acceptable salts and solvates which act as phosphodiesterse VII inhibitors and are thus useful for the treatment of allergic disorders, asthma, chronic bronchitis, atopic dermatitis, psoriasis and other skin disorders, inflammatory disorders, autoimmune diseases, rheumatoid arthritis, multiple sclerosis, Crohn's disease, diabetes mellitus or ulcerative colitis, osteoporosis, transplant rejection reactions, cachexia, tumor growth, tumor metastases, sepsis, memory disturbances, atherosclerosis and AIDS.

20 Claims, No Drawings

ISOXAZOLE DERIVATIVES TO BE USED AS PHOSPHODIESTERASE VII INHIBITORS

This application is a 371 of PCT/EP00/10239 filed Oct. 18, 2000.

The invention relates to compounds of formula I

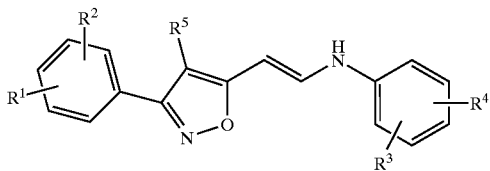

in which

R$^1$, R$^2$, R$^3$, R$^4$ are each, independently of one another, Hal, OA$^1$, SA$^1$, A, H, COOA$^1$, CN or CONA$^1$A$^2$, R$^5$ is COOA$^1$, CN or CONA$^1$A$^2$, A$^1$, A$^2$ are each, independently of one another, H, A, alkenyl, cycloalkyl or alkylenecycloalkyl, A is alkyl having 1 to 10 C atoms, Hal is F, Cl, Br or I, and their physiologically acceptable salts and/or solvates as phosphodiesterase VII inhibitors.

The invention further relates to the use of the compounds of the formula I for producing a pharmaceutical for controlling allergic disorders, asthma, chronic bronchitis, atopic dermatitis, psoriasis and other skin disorders, inflammatory disorders, autoimmune diseases such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

Compounds of the formula I are described by Bionet.

The invention was based on the object of finding novel compounds with valuable properties, in particular those which can be used for producing pharmaceuticals.

It has been found that the compounds of the formula I and their salts have very valuable pharmacological properties while being well tolerated. In particular, they show a specific inhibition of the "rolipram-insensitive" cAMP phosphodiesterase (PDE VII).

The biological activity of the compounds of the formula I can be determined by methods like those described, for example, by M. A. Giembycz et al. in Br. J. Pharmacol. (1996), 118, 1945–1958. The affinity of the compounds for cAMP phosphodiesterase (PDE VII) is determined by measuring their IC$_{50}$ values (concentration of the inhibitor required to achieve 50% inhibition of the enzymic activity). The determinations were carried out using homogenized SK-N-SH neuroblastoma cells in place of T lymphocytes, and CI-930 was employed to inhibit PDE III. The latter is a selective PDE III inhibitor (J. A. Bristol et al., J. Med. Chem. 1984, 27(9), 1099–1101).

The compounds of the formula I can be employed for treating asthmatic disorders. The antiasthmatic effect can be determined, for example, in analogy to the method of T. Olsson, Acta allergologica 26, 438–447 (1971).

Since cAMP inhibits osteoclastic cells and stimulates osteoblastic cells (S. Kasugai et al., M 681 and K. Miyamoto, M 682, in Abstracts of the American Society for Bone and Mineral Research 18th Annual Meeting, 1996), the compounds of the formula I can be employed for treating osteoporosis.

The compounds additionally show an antagonistic effect on the production of TNFα (tumour necrosis factor) and are therefore suitable for treating allergic and inflammatory disorders, autoimmune diseases such as, for example, rheumatoid arthritis, multiple sclerosis, Crohn's disease, diabetes mellitus or ulcerative colitis, transplant rejection reactions, cachexia and sepsis.

The antiinflammatory effect of the substances of the formula I and their efficacy for the treatment of, for example, autoimmune diseases such as multiple sclerosis or rheumatoid arthritis can be determined in analogy to the methods of N. Sommer et al., Nature Medicine 1, 244–248 (1995) or L. Sekut et al., Clin. Exp. Immunol. 100, 126–132 (1995).

The compounds can be employed for treating cachexia. The anti-cachectic effect can be tested in TNF-dependent models of cachexia (P. Costelli et al., J. Clin. Invest. 95, 2367ff. (1995); J. M. Argiles et al., Med. Res. Rev. 17, 477ff. (1997)).

The PDE VII inhibitors are also able to inhibit the growth of tumour cells and are therefore suitable for tumour therapy (for PDE IV inhibitors, cf. D. Marko et al., Cell Biochem. Biophys. 28, 75ff. (1998)).

They can furthermore be employed for the therapy of sepsis and for treating memory disturbances, atherosclerosis, atopic dermatitis and AIDS, and for treating T-cell-dependent diseases (L. Li et al., Science, 1999, 283, 848–851).

The invention further relates to the use of phosphodiesterase VII inhibitors for producing a pharmaceutical for controlling allergic disorders, asthma, chronic bronchitis, atopic dermatitis, psoriasis and other skin disorders, inflammatory disorders, autoimmune diseases such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

The compounds of the formula I can be employed as active pharmaceutical ingredients for inhibiting PDE VII in human and veterinary medicine.

A is alkyl having 1–10 C atoms and has 1, 2, 3, 4, 5, 6, 7, 8, 9 or 10 C atoms and is preferably methyl, ethyl or propyl, also preferably isopropyl, butyl, isobutyl, sec-butyl or tert-butyl, but is also n-pentyl, neopentyl, isopentyl or hexyl. It is also possible for 1–7 H atoms in the radicals to be replaced by F and/or Cl. A is therefore also, for example, trifluoromethyl or pentafluoroethyl.

Cycloalkyl has 3–9 C atoms and is preferably, for example, cyclopentyl or cyclohexyl. Alkenyl has 2–10 C atoms, is linear or branched and is preferably vinyl, propenyl or butenyl.

Alkylenecycloalkyl has 4–10 C atoms and is, for example methylenecyclopentyl, ethylenecyclopentyl, methylenecyclohexyl or ethylenecyclohexyl.

Accordingly, the invention relates in particular to those compounds of the formula I as phosphodiesterase VII inhibitors in which at least one of the said radicals has one of the preferred meanings indicated above. Some preferred groups of compounds can be expressed by the following part-formulae Ia to Ig which correspond to formula I and in which the undefined radicals have the meaning stated for formula I, but in which in Ia R$^1$ is H;

in Ib

R$^1$ and R$^2$ are H;

in Ic
  $R^1$ is H and
  $R^2$ is F or Cl;
in Id
  $R^1$, $R^2$ are each, independently of one another, H or Hal;
in Ie
  $R^1$, $R^2$ are each, independently of one another, H or Hal,
  $A^1$, $A^2$ are each, independently of one another, H or A;
in If
  $A^1$, $A^2$ are each, independently of one another, H or A;
in Ig
  $R^1$, $R^2$ are each, independently of one another, H or Hal,
  $A^1$, $A^2$ are each, independently of one another, H or A,
  A is alkyl having 1, 2, 3 or 4 C atoms,
  Hal is F or Cl.

A base of the formula I can be converted with an acid into the relevant acid addition salt, for example by reacting equivalent amounts of the base and the acid in an inert solvent such as ethanol and subsequently evaporating. Acids particularly suitable for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, also organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, maleic acid, citric acid, gluconic acid, ascorbic acid, nicotinic acid, isonicotinic acid, methane- or ethanesulfonic acid, ethanedisulfonic acid, 2-hydroxy-ethanesulfonic acid, benzenesulfonic acid, p-toluene-sulfonic acid, naphthalenemono- and -disulfonic acids, lauryl sulfuric acid. Salts with physiologically unacceptable acids, for example picrates, can be used to isolate and/or purify the compounds of the formula I.

The invention furthermore relates to pharmaceutical preparations comprising at least one phosphodiesterase VII inhibitor of the formula I and/or one of its physiologically acceptable salts and/or solvates for controlling allergic disorders, asthma, chronic bronchitis, atopic dermatitis, psoriasis and other skin disorders, inflammatory disorders, autoimmune diseases such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

This preferably entails the substances being administered in dosages between about 1 and 500 mg, in particular between 5 and 100 mg, per dosage unit. The daily dose is preferably between about 0.02 and 10 mg/kg of body weight. The specific dose for each patient depends on a wide variety of factors, however, for example on the efficacy of the specific compound employed, on the age, body weight, general state of health, sex, on the diet, on the time and route of administration, on the rate of excretion, medicinal substance combination and severity of the particular disorder to which the therapy applies. Oral administration is preferred.

The pharmaceutical preparations can be used as pharmaceuticals in human or veterinary medicine. Suitable carriers are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. In particular, tablets, pills, coated tablets, capsules, powders, granules, syrups, suspensions or drops are used for oral administration, suppositories for rectal administration, solutions, preferably oily or aqueous solutions, also suspensions, emulsions or implants, for parenteral administration, ointments, creams or dusting powders for topical administration. The novel compounds can also be lyophilized, and the resulting lyophilizates can be used, for example, to manufacture products for injection. The stated preparations can be sterilized and/or comprise excipients such as lubricants, preservatives, stabilizers and/or wetting agents, emulsifiers, salts to influence the osmotic pressure, buffer substances, colouring agents, flavourings and/or several other active ingredients, for example one or more vitamins.

The invention particularly relates to the compounds of the formula I listed in the following examples, and their physiologically acceptable salts and/or solvates as PDE VII inhibitors, and to the use thereof for producing a pharmaceutical for controlling allergic disorders, asthma, chronic bronchitis, atopic dermatitis, psoriasis and other skin disorders, inflammatory disorders, autoimmune diseases such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

EXAMPLES

5-[2-(2-Fluoro-4-hydroxyphenylamino)vinyl]-4-cyano-3-phenylisoxazole,
5-[2-(2,4-Difluorophenylamino)vinyl]-4-cyano-3-phenylisoxazole,
5-[2-(3-Methylthiophenylamino)vinyl]-4-cyano-3-phenylisoxazole,
5-[2-(2,4-Dimethoxyphenylamino)vinyl]-4-cyano-3-(2-chlorophenyl)isoxazole,
5-(2-Amino-2-phenylvinyl)-4-methylaminocarbonyl-3-phenylisoxazole,
5-(2-Phenylaminovinyl)-4-methoxycarbonyl-3-phenylisoxazole,
5-[2-(4-Carboxyphenylamino)vinyl]-4-cyano-3-phenylisoxazole,
5-[2-(4-Carboxyphenylamino)vinyl]-4-methoxycarbonyl-3-phenylisoxazole,
5-[2-(5-Chloro-2-hydroxyphenylamino)vinyl]-4-cyano-3-phenylisoxazole,
5-[2-(3,4-Dimethylphenylamino)vinyl]-4-cyano-3-(2-chlorophenyl)isoxazole,
5-[2-(4-Chlorophenylamino)vinyl]-4-cyano-3-(2-chlorophenyl)isoxazole,
5-(2-Phenylaminovinyl)-4-cyano-3-(2-chlorophenyl)isoxazole,
5-[2-(4-Methoxyphenylamino)vinyl]-4-cyano-3-(2-chlorophenyl)isoxazole,
5-[2-(4-Carboxyphenylamino)vinyl]-4-cyano-3-(2-chlorophenyl)isoxazole,
5-[2-(2-Fluoro-4-hydroxyphenylamino)vinyl]-4-cyano-3-(2-chlorophenyl)isoxazole,
5-[2-(4-Fluorophenylamino)vinyl]-4-cyano-3-(2-chlorophenyl)isoxazole,
5-[2-(3,5-Dichlorophenylamino)vinyl]-4-cyano-3-(2-chlorophenyl)isoxazole,
5-[2-(3-Chlorophenylamino)vinyl]-4-cyano-3-(2-chlorophenyl)isoxazole, 5-(2-Phenylaminovinyl)-4-cyano-3-(2,6-dichlorophenyl) isoxazole,
5-[2-(4-Chlorophenylamino)vinyl]-4-cyano-3-(2,6-dichlorophenyl)isoxazole,
5-(2-Phenylaminovinyl)-4-methoxycarbonyl-3-(2,6-dichlorophenyl)isoxazole,
5-[2-(4-Chlorophenylamino)vinyl]-4-methoxycarbonyl-3-(2,6-dichlorophenyl)isoxazole,
5-[2-(4-Carboxyphenylamino)vinyl]-4-methoxycarbonyl-3-(2,6-dichlorophenyl)isoxazole,
5-[2-(2,4-Difluorophenylamino)vinyl]-4-cyano-3-(2,6-dichlorophenyl)isoxazole,
5-[2-(2,4-Dichlorophenylamino)vinyl]-4-cyano-3-(2,6-dichlorophenyl)isoxazole,
5-[2-(4-Carboxyphenylamino)vinyl]-4-cyano-3-(2,6-dichlorophenyl)isoxazole,
5-[2-(3,5-Dichlorophenylamino)vinyl]-4-cyano-3-(2,6-dichlorophenyl)isoxazole,
5-[2-(4-Methoxyphenylamino)vinyl]-4-cyano-3-(2,6-dichlorophenyl)isoxazole,
5-[2-(2,4-Dimethoxyphenylamino)vinyl]-4-cyano-3-(2,6-dichlorophenyl)isoxazole,
5-[2-(2-Phenylphenylamino)vinyl]-4-cyano-3-(2,6-dichlorophenyl)isoxazole,
5-[2-(4-Methylphenylamino)vinyl]-4-cyano-3-(2,6-dichlorophenyl)isoxazole,
5-(2-Phenylaminovinyl)-4-cyano-3-(2-chloro-6-fluorophenyl)isoxazole,
5-[2-(4-Carboxyphenylamino)vinyl]-4-cyano-3-(2-chloro-6-fluorophenyl)isoxazole,
5-[2-(4-Chlorophenylamino)vinyl]-4-cyano-3-(2-chloro-6-fluorophenyl)isoxazole,
5-[2-(3-Methoxyphenylamino)vinyl]-4-cyano-3-(2-chloro-6-fluorophenyl)isoxazole,
5-[2-(4-Chlorophenylamino)vinyl]-4-methoxycarbonyl-3-(2-chloro-6-fluorophenyl)isoxazole,
5-(2-Phenylaminovinyl)-4-methoxycarbonyl-3-(2-chloro-6-fluorophenyl)isoxazole,
5-[2-(2,4-Dichlorophenylamino)vinyl]-4-methoxycarbonyl-3-(2-chloro-6-fluorophenyl)isoxazole,
5-(2-Phenylaminovinyl)-4-cyano-3-phenylisoxazole,
5-[2-(3-Trifluoromethoxyphenylamino)vinyl]-4-cyano-3-phenylisoxazole,
5-[2-(4-Methoxyphenylamino)vinyl]-4-cyano-3-phenylisoxazole,
5-[2-(4-Methoxyphenylamino)vinyl]-4-methoxycarbonyl-3-(2-chloro-6-fluorophenyl)isoxazole,
5-[2-(3-Methylthiophenylamino)vinyl]-4-cyano-3-phenylisoxazole,
5-[2-(2,4-Difluorophenylamino)vinyl]-4-cyano-3-phenylisoxazole,
5-[2-(2-Fluoro-4-hydroxyphenylamino)vinyl]-4-cyano-3-phenylisoxazole.

The following examples relate to pharmaceutical preparations:

Example A

Vials

A solution of 100 g of a phosphodiesterase VII inhibitor of the formula I and 5 g of disodium hydrogen phosphate in 3 l of double-distilled water is adjusted to pH 6.5 with 2 N hydrochloric acid, sterilized by filtration, dispensed into vials, lyophilized under sterile conditions and sealed sterile. Each vial comprises 5 mg of active ingredient.

Example B

Suppositories

A mixture of 20 g of a phosphodiesterase VII inhibitor of the formula I with 100 g of soya lecithin and 1400 g of cocoa butter is melted, poured into moulds and left to cool. Each suppository comprises 20 mg of active ingredient.

Example C

Solution

A solution is prepared from 1 g of a phosphodiesterase VII inhibitor of the formula I, 9.38 g of $NaH_2PO_4.2H_2O$, 28.48 g of $Na_2HPO_4.12H_2O$ and 0.1 g of benzalkonium chloride in 940 ml of double-distilled water. The pH is adjusted to 6.8, the volume is made up to 1 l, and the solution is sterilized by irradiation. This solution can be used in the form of eye drops.

Example D

Ointment 500 mg of a phosphodiesterase VII inhibitor of the formula I are mixed with 99.5 g of petrolatum under aseptic conditions.

Example E

Tablets

A mixture of 1 kg of phosphodiesterase VII inhibitor of the formula I, 4 kg of lactose, 1.2 kg of potato starch, 0.2 kg of talc and 0.1 kg of magnesium stearate is compressed to tablets in a conventional way so that each tablet comprises 10 mg of active ingredient.

Example F

Coated Tablets

Tablets are compressed in analogy to Example E and are then coated in a conventional way with a coating of sucrose, potato starch, talc, tragacanth and colouring agent.

Example G

Capsules 2 kg of phosphodiesterase VII inhibitor of the formula I are packed into hard gelatin capsules in a conventional way so that each capsule comprises 20 mg of the active ingredient.

Example H

Ampoules

A solution of 1 kg of phosphodiesterase VII inhibitor of the formula I in 60 l of double-distilled water is sterilized by filtration, dispensed into ampoules, lyophilized under sterile conditions and sealed sterile. Each ampoule comprises 10 mg of active ingredient.

Example I

Spray for Inhalation 14 g of phosphodiesterase VII inhibitor of the formula I are dissolved in 10 l of isotonic NaCl solution, and the solution is dispensed into commercial spray vessels with a pump mechanism. This solution can be sprayed into the mouth or nose. One spray actuation (about 0.1 ml) corresponds to a dose of about 0.14 mg.

What is claimed is:
1. A compound of formula I

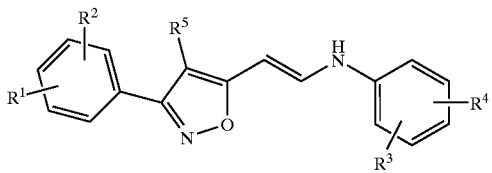

wherein
$R^1$, $R^2$, $R^3$, and $R^4$ are each, independently of one another, Hal, $OA^1$, $SA^1$, A, H, $COOA^1$, CN or $CONA^1A^2$,
$R^5$ is $COOA^1$, CN or $CONA^1A^2$,
$A^1$, and $A^2$ are each, independently of one another, H, A, alkenyl, cycloalkyl or alkylenecycloalkyl,
A is alkyl having 1 to 10 C atoms that is optionally substituted by 1 to 7 F or Cl or F and Cl atoms, and
Hal is F, Cl, Br or I,
or a physiologically acceptable salt or solvate thereof.

2. A pharmaceutical composition comprising a compound of formula I according to claim 1 or a physiologically acceptable salt or solvate thereof and a pharmaceutically acceptable carrier.

3. A method of treating an allergic disorder, asthma, chronic bronchitis, atopic dermatitis, psoriasis, a skin disorder other than psoriasis, an inflammatory disorder, an autoimmune disease, rheumatoid arthritis, multiple sclerosis, Crohn's disease, diabetes mellitus, ulcerative colitis, osteoporosis, a transplant rejection reaction, cachexia, a tumor growth or a tumor metastases, sepsis, a memory disturbance, atherosclerosis or AIDS comprising administering an effective amount of a pharmaceutical composition of claim 2 to a patient in need thereof.

4. A method of inhibiting phosphodiesterase VII comprising administering an effective amount of a pharmaceutical composition of claim 2 to a patient in need thereof.

5. A method of treating asthma comprising administering an effective amount of a pharmaceutical composition of claim 2 to a patient in need thereof.

6. A method of treating osteoporosis comprising administering an effective amount of a pharmaceutical composition of claim 2 to a patient in need thereof.

7. A method of treating cachexia comprising administering an effective amount of a pharmaceutical composition of claim 2 to a patient in need thereof.

8. A compound according to claim 1 wherein A is methyl, ethyl, propyl. isopropyl, butyl, isobutyl, sec-butyl, tert-butyl, n-pentyl, neopentyl, isopentyl, hexyl, trifluoromethyl or pentafluoroethyl, and wherein cycloalkyl has 3–9 C atoms, and wherein alkenyl has 2–10 C atoms and is linear or branched, and wherein alkylenecycloalkyl has 4–10 C atoms.

9. A compound according to claim 1 wherein cycloalkyl is cyclopentyl or cyclohexyl, and wherein alkenyl is preferably vinyl, propenyl or butenyl, and wherein alkylenecycloalkyl is methylenecyclopentyl, ethylenecyclopentyl, methylenecyclohexyl or ethylenecyclohexyl.

10. A compound according to claim 1, wherein $R^1$ is H.
11. A compound according to claim 1, wherein $R^1$ and $R^2$ are H.
12. A compound according to claim 1, wherein $R^1$ is H and $R^2$ is F or Cl.
13. A compound according to claim 1, wherein $R^1$ and $R^2$ are each, independently of one another, H or Hal.
14. A compound according to claim 1, wherein $R^1$ and $R^2$ are each, independently of one another, H or Hal, and $A^1$ and $A^2$ are each independently of one another, H or A.
15. A compound according to claim 1, wherein $A^1$ and $A^2$ are each, independently of one another, H or A.
16. A compound according to claim 1, wherein $R^1$ and $R^2$ are each, independently of one another, H or Hal, $A^1$ and $A^2$ are each, independently of one another, H or A, A is alkyl having 1, 2, 3 or 4 C atoms, and Hal is F or Cl.
17. A compound according to claim 1, wherein the compound of formula I is selected from the group consisting of
5-[2-(2-Fluoro-4-hydroxyphenylamino)vinyl]-4-cyano-3-phenylisoxazole,
5-[2-(2,4-Difluorophenylamino)vinyl]-4-cyano-3-phenylisoxazole,
5-[2-(3-Methylthiophenylamino)vinyl]-4-cyano-3-phenylisoxazole,
5-[2-(2,4-Dimethoxyphenylamino)vinyl]-4-cyano-3-(2-chlorophenyl)isoxazole,
5-(2-Amino-2-phenylvinyl)-4-methylaminocarbonyl-3-phenylisoxazole,
5-(2-Phenylaminovinyl)-4-methoxycarbonyl-3-phenylisoxazole,
5-[2-(4-Carboxyphenylamino)vinyl]-4-cyano-3-phenylisoxazole,
5-[2-(4-Carboxyphenylamino)vinyl]-4methoxycarbonyl-3-phenylisoxazole,
5-[2-(5-Chloro-2-hydroxyphenylamino)vinyl]-4-cyano-3-phenylisoxazole,
5-[2-(3,4-Dimethylphenylamino)vinyl]-4-cyano-3-(2-chlorophenyl)isoxazole,
5-[2-(4-Chlorophenylamino)vinyl]-4-cyano-3-(2-chlorophenyl)isoxazole,
5-(2-Phenylaminovinyl)-4-cyano-3-(2-chlorophenyl)isoxazole,
5-[2-(4-Methoxyphenylamino)vinyl]-4-cyano-3-(2-chlorophenyl)isoxazole,
5-[2-(4-Carboxyphenylamino)vinyl]-4-cyano-3-(2-chlorophenyl)isoxazole,
5-[2-(2-Fluoro-4-hydroxyphenylamino)vinyl]-4-cyano-3-(2-chlorophenyl)isoxazole,
5-[2-(4-Fluoropheoylamino)vinyl]-4-cyano-3-(2chlorophenyl)isoxazole,
5-[2-(3,5-Dichlorophenylamino)vinyl]-4-cyano-3-(2-chlorophenyl)isoxazole,
5-[2-(3-Chlorophenylamino)vinyl]-4-cyano-3-(2-chlorophenyl)isoxazole,
5-(2-Phenylaminovinyl)-4-cyano-3-(2,6-dichlorophenyl)isoxazole,
5-[2-(4-Chlorophenylamino)vinyl]-4-cyano-3-(2,6-dichlorophenyl)isoxazole,
5-(2-Phenylaminovinyl)-4-methoxycarbonyl-3-(2,6-dichlorophenyl)isoxazole,
5-[2-(4-Chlorophenylamino)vinyl]-4-methoxycarbonyl-3-(2,6-dichlorophenyl)isoxazole,
5-[2-(4-Carboxyphenylamino)vinyl]-4-methoxycarbonyl-3-(2,6-dichlorophenyl)isoxazole,
5-[2-(2,4-Difluorophenylamino)vinyl]-4-cyano-3-(2,6-dichlorophenyl)isoxazole,
5-[2-(2,4-Dichlorophenylamino)vinyl]-4-cyano-3-(2,6-dichlorophenyl)isoxazole,
5-[2-(4-Carboxyphenylamino)vinyl]-4-cyano-3-(2,6-dichlorophenyl)isoxazole,
5-[2-(3,5-Dichlorophenylamino)vinyl]-4-cyano-3-(2,6-dichlorophenyl)isoxazole,
5-[2-(4-Methoxyphenylamino)vinyl]-4-cyano-3-(2,6-dichlorophenyl)isoxazole, 5-[2-(2,4-Dimethoxyphenylamino)vinyl]-4-cyano-3-(2,6-dichlorophenyl)isoxazole,
5-[2-(2-Phenylphenylamino)vinyl]-4-cyano-3-(2,6-dichlorophenyl)isoxazole,
5-[2-(4-Methylphenylamino)vinyl]-4-cyano-3-(2,6-dichlorophenyl)isoxazole,
5-(2-Phenylaminovinyl)-4-cyano-3-(2-chloro-6-fluorophenyl)isoxazole,
5-[2-(4-Carboxyphenylamino)vinyl]-4-cyano-3-(2-chloro-6-fluorophenyl)isoxazole,
5-[2-(4-Chlorophenylamino)vinyl]-4-cyano-3-(2-chloro-6-fluorophenyl)isoxazole,
5-[2-(3-Methoxyphenylamino)vinyl]-4-cyano-3-(2-chloro-6-fluorophenyl)isoxazole,
5-[2-(4-Chlorophenylamino)vinyl]-4-methoxycarbonyl-3-(2-chloro-6-fluorophenyl)isoxazole,
5-(2-Phenylaminovinyl)-4-methoxycarbonyl-3-(2-chloro-6-fluorophenyl)isoxazole,
5-[2-(2,4-Dichlorophenylamino)vinyl]-4-methoxycarbonyl-3-(2-chloro-6-fluorophenyl)isoxazole,
5-(2-Phenylaminovinyl)-4-cyano-3-phenylisoxazole,
5-[2-(3-Trifluoromethoxyphenylamino)vinyl]-4-cyano-3-phenylisoxazole,
5-[2-(4-Methoxyphenylamino)vinyl]-4-cyano-3-phenylisoxazole,
5-[2-(4-Methoxyphenylamino)vinyl]-4-methoxycarbonyl-3-(2-chloro-6-fluorophenyl)isoxazole,
5-[2-(3-Methylthiophenylamino)vinyl]-4-cyano-3-phenylisoxazole,
5-[2-(2,4-Difluorophenylamino)vinyl]-4-cyano-3-phenylisoxazole, and
5-[2-(2-Fluoro-4-hydroxyphenylamino)vinyl]-4-cyano-3-phenylisoxazole.

18. A method according to claim 3, wherein the patient is a human or an animal.

19. A method according to claim 3, wherein administration is oral administration.

20. A method for antagonizing the production of TNFα comprising administering an effective amount of a pharmaceutical composition of claim 2 to a patient in need thereof.

* * * * *

UNITED STATES PATENT AND TRADEMARK OFFICE
CERTIFICATE OF CORRECTION

PATENT NO. : 6,531,498 B1
DATED : March 11, 2003
INVENTOR(S) : Hans-Michael Eggenweiler et al.

It is certified that error appears in the above-identified patent and that said Letters Patent is hereby corrected as shown below:

Column 7,
Line 50, reads "propyl. isopropyl," should read -- propyl, isopropyl, --

Column 8,
Line 26, reads "-4methoxycarbonyl-" should read -- 4-methoxycarbonyl --
Line 42, reads "(4-Fluoropheoylamino)" should read -- (4-Fluorophenylamino) --
Line 43, reads "(2chlorophenyl)" should read -- (2-chlorophenyl) --

Signed and Sealed this

Eighteenth Day of May, 2004

JON W. DUDAS
*Acting Director of the United States Patent and Trademark Office*